United States Patent [19]
Doying, Sr. et al.

[11] Patent Number: 5,865,811
[45] Date of Patent: Feb. 2, 1999

[54] MULTI-DOSE APPLICATOR WITH QUICK BOTTLE ATTACHMENT MECHANISM

[75] Inventors: Dean Doying, Sr., Victoria, Minn.; Tom Kennedy, Mundelein, Ill.; Wayne Cole, St. Joseph, Mo.; W. L. Eidson, Minneapolis, Minn.; Jack Zupan, Yarley, Pa.

[73] Assignee: Boehringer Ingelheim Vetmedica, Inc., St. Joseph, Mo.

[21] Appl. No.: 968,359

[22] Filed: Nov. 12, 1997

Related U.S. Application Data

[63] Continuation of Ser. No. 33,475, Dec. 19, 1996.

[60] Provisional application No. 60/033,475 Dec. 19, 1996.

[51] Int. Cl.[6] ............................. A61M 5/178; A61M 5/00
[52] U.S. Cl. ............................................. 604/183; 604/187
[58] Field of Search .................................. 604/187, 183, 604/181, 240, 131, 242, 241, 243, 134, 135, 152, 154, 191; 222/325, 82, 88, 321.7, 383.1

[56] References Cited

U.S. PATENT DOCUMENTS

| | | | |
|---|---|---|---|
| 3,908,651 | 9/1975 | Fudge | 604/183 |
| 4,564,360 | 1/1986 | Young et al. | 604/183 |

*Primary Examiner*—Wynn Wood Coggins
*Assistant Examiner*—Michael J Hayes
*Attorney, Agent, or Firm*—R. P. Raymond; M-E. M. Devlin; A. R. Stempel

[57] ABSTRACT

A multi-dose applicator comprising a bottle locking assembly wherein a supply bottle can be quickly and easily attached or removed from the applicator by rotating a locking ring a fraction of a turn and wherein the plunger is flexible to allow for misalignment.

9 Claims, 5 Drawing Sheets

MULTI-DOSE APPLICATOR WITH QUICK BOTTLE ATTACHMENT MECHANISM

RELATED APPLICATIONS

This application is a continuation of prior provisional application Ser. No. 60/033,475, filed Dec. 19, 1996.

FIELD OF THE INVENTION

This invention relates a reliable compact multidose applicator which comprises a bottle attachment assembly that allows quick and easy removal and attachment of a supply bottle to the applicator and a plunger assembly that flexes to compensate for any possible misalignment or tolerance accumulation.

BACKGROUND OF THE INVENTION

Drug applicators such as syringes and drenchers have long been known in the industry. Some of the prior art multi-dose applicators are described in U.S. Pat. Nos. 5,232,459, 5,188,610, 4,738,664, 4,245,757, and 4,020,838 and in the N.J. Phillips 1986 Export Catalogue which are incorporated herein by reference.

Generally, the prior applicators employed a threaded nut screw for attaching the applicator to a drug supply. The use of threaded nut screws for attaching the drug supply to an applicator is time consuming and cumbersome, especially when entire herds of cattle or sheep are being treated.

The prior applicators such as those described in U.S. Pat. Nos. 4,738,664, 4,245,757 and 4,020,838 all possess plunger assemblies that comprise a shaft of a uniform diameter. The uniform diameter shafts fail to compensate for any misalignment of the plunger with the dosage tube or tolerance accumulation.

SUMMARY OF THE INVENTION

It is an objective of the present invention to provide an applicator wherein the drug supply can be quickly and easily attached and removed from the applicator.

It is also an objective of the present invention to provide an applicator wherein the plunger assembly compensates for any possible misalignment or tolerance accumulation.

The foregoing objectives are met by a drug applicator comprising a body comprising a front portion and a rear portion wherein the front portion is slidably connected to the rear portion; a needle assembly attached to the front portion of the body; a dosage tube attached to the front portion of the body and connected to the needle assembly by a passageway within the front portion of the body; a plunger assembly attached to the rear portion of the body and slidably located within the dosage tube; and a bottle locking assembly attached to either the front or rear portion of the body.

The bottle locking assembly comprises: a locking ring comprising a side wall, an end wall with an aperture in the end wall, and protrusions that extend inwardly from the side wall; a bottle holder that is sized to fit within the side wall of the locking ring and comprising a base with an aperture and a plurality of flanges that extend upwardly from the base; and a supply needle assembly comprising a fluid intake needle for withdrawing fluid from a supply bottle into the dosage tube of the applicator. The locking ring rotates around the bottle holder and the protrusions of the locking ring contact and compress the flanges of the bottle holder to secure the supply bottle to the applicator.

The locking ring is preferably cup shaped with the aperture in the bottom of the cup.

The bottle holder is sized to fit within the area defined by the side wall of the locking ring so that the locking ring can be rotated around the bottle holder.

The supply needle assembly attaches to the applicator by passing through the aperture in the base of the bottle holder and through the aperture in the end wall of the locking ring. The supply needle assembly also functions to secure the locking ring and bottle holder to the applicator and each other. The supply needle assembly is also connected to the dosage tube by a passageway in the applicator.

The drug or supply bottle is quickly and easily released from the applicator by rotating the locking ring clockwise until the protrusions of the locking ring are disengaged from the flanges of the bottle holder and the flanges expand to their normal shape and position. Once the flanges are in their normal position, the drug or supply bottle may be removed from the applicator.

The engagement/disengagement of the protrusions on the locking ring with the bottle holder flanges may occur every half, third, quarter or other fraction of a complete rotation of the locking ring. It is preferred that the engagement/disengagement occur every third or quarter rotation of the locking ring.

The plunger assembly of the present invention comprises a plunger and a plunger shaft that comprises a thin section and a thick section. The plunger is made from a plastic material such as polycarbonate which will allow the thin section of the plunger shaft to flex and thereby compensate for any misalignment or tolerance accumulation in the plunger assembly. The plastic material will also impart a memory or resilient property to the plunger shaft so that the plunger will attempt to realign the applicator and serve to maintain a positive spring alignment.

DETAILED DESCRIPTION OF A PREFERRED EMBODIMENT

The present invention will be described in detail by reference to the drawings. The drawings are for illustration and are not intended to limit the scope of the invention.

Figure 1:
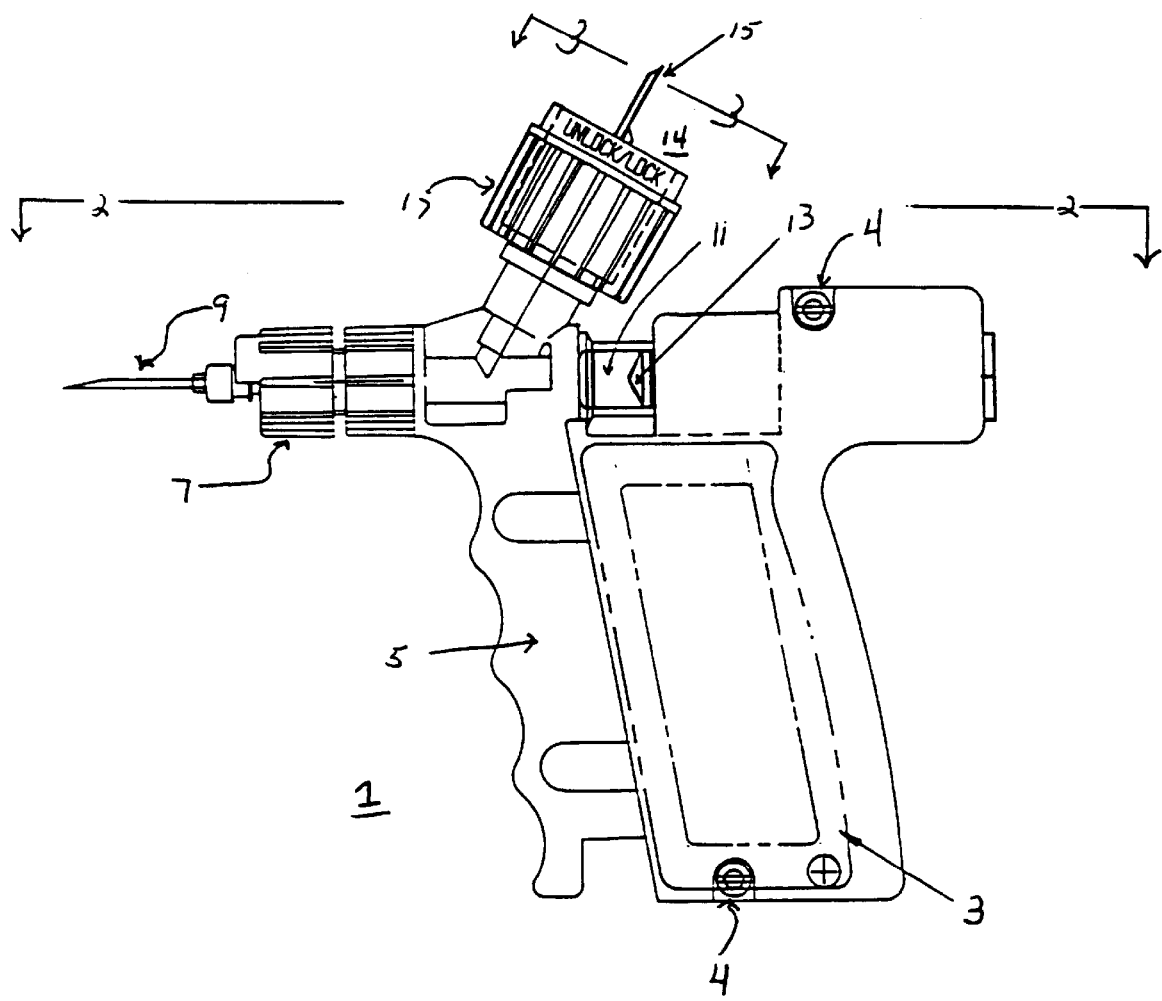
FIG. 1 is a side plan view of a preferred embodiment of the present invention.
Figure 2:
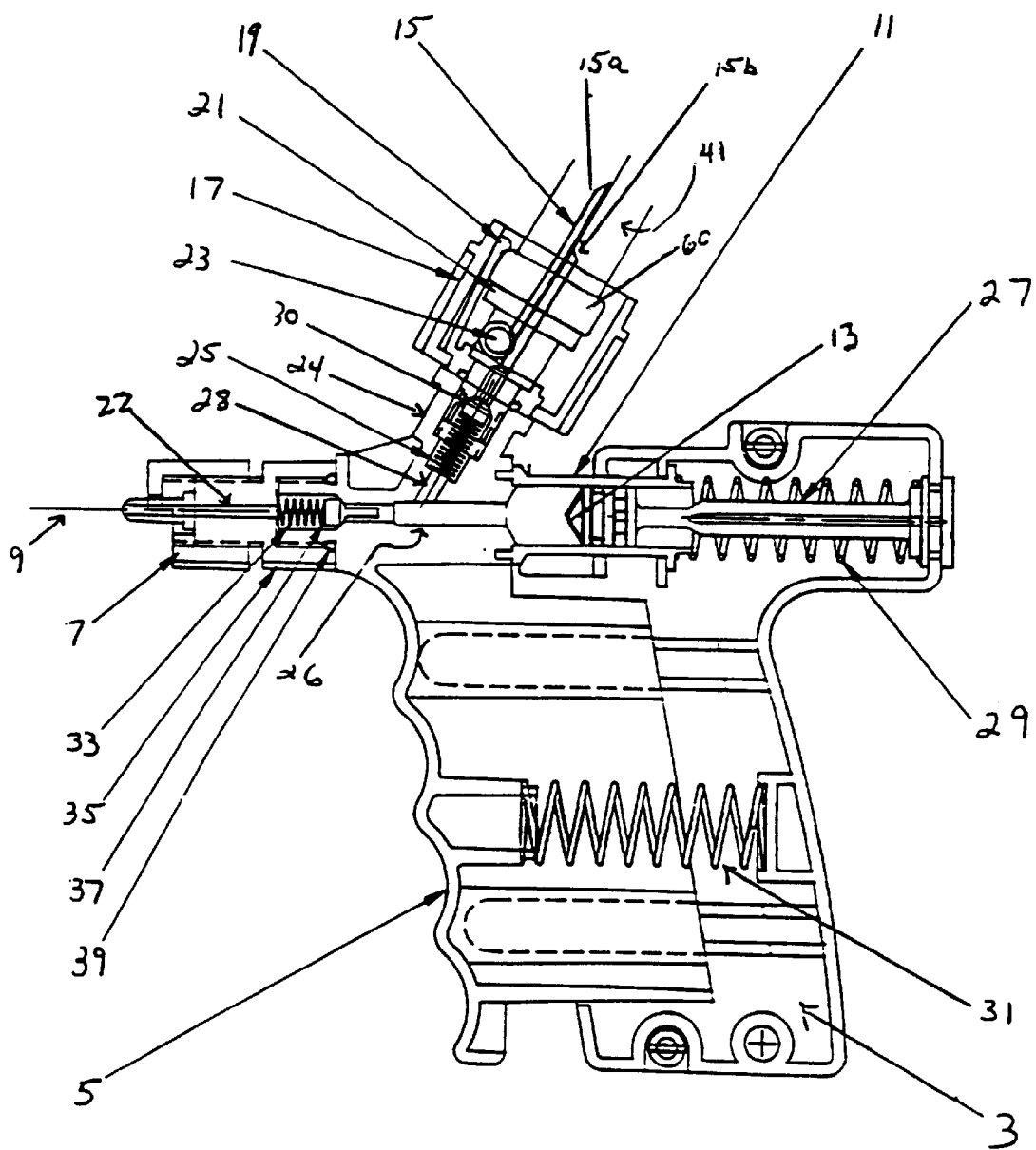
FIG. 2 is a cut away side view of a preferred embodiment of the present invention taken along line 2—2 of FIG. 1.
Figure 3:
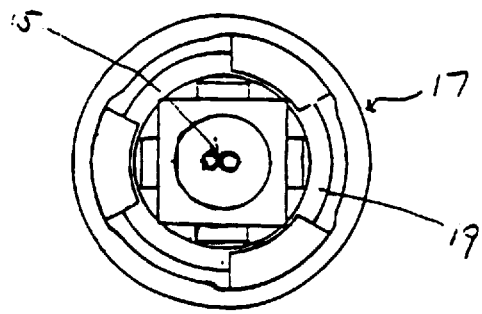
FIG. 3 is a top view of a preferred embodiment of the bottle attachment assembly of the present invention taken along line 3—3 of FIG. 1.
Figure 4:
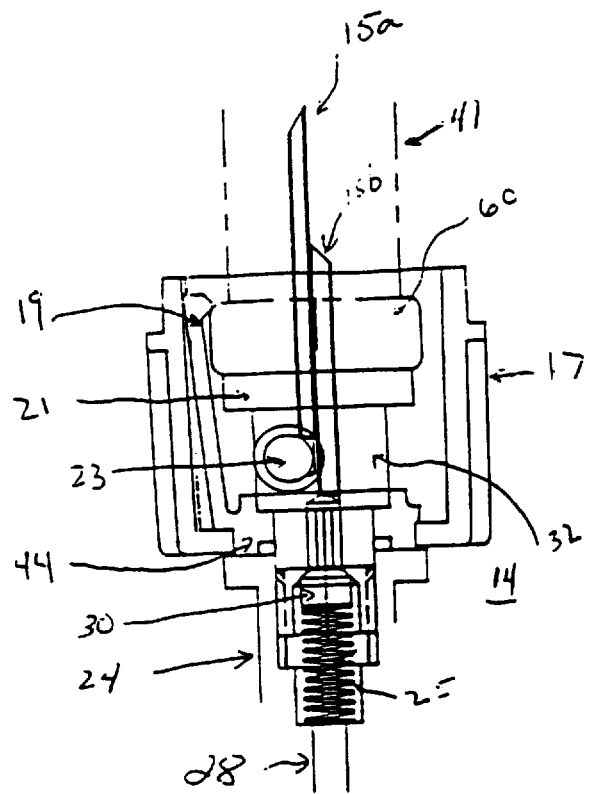
FIG. 4 is an expanded side cut away view of a preferred embodiment of the bottle attachment assembly of the present invention as shown in FIG. 2.
Figure 5:
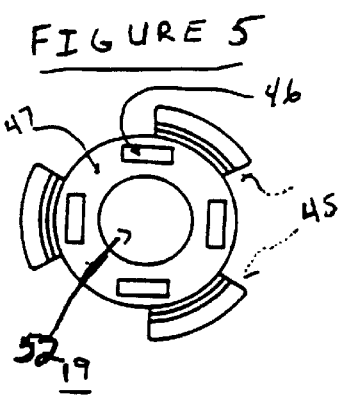
FIG. 5 is a top isolated view of a preferred embodiment of the bottle holder of the present invention.
Figure 6:
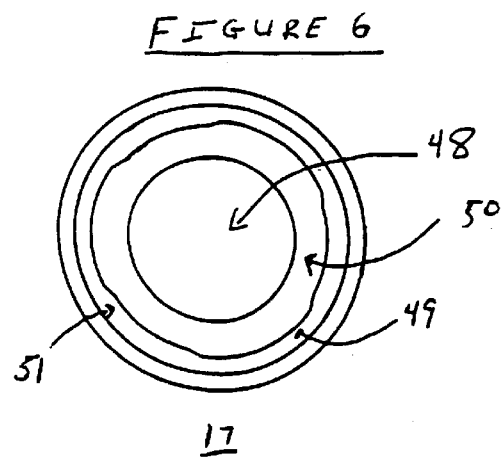
FIG. 6 is a top isolated view of a preferred embodiment of the locking ring of the present invention.
Figure 7:
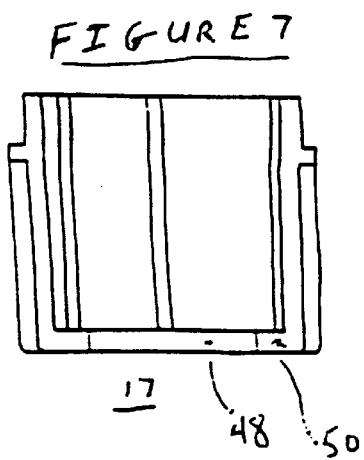
FIG. 7 is an expanded side cut away view of a preferred embodiment of the locking ring of the present invention.
Figure 8:
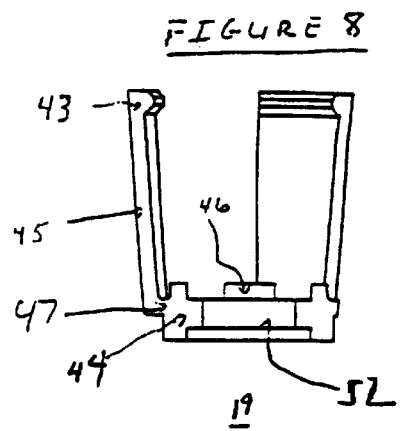
FIG. 8 is an expanded side cut away view of a preferred embodiment of the bottle holder of the present invention.
Figure 9:
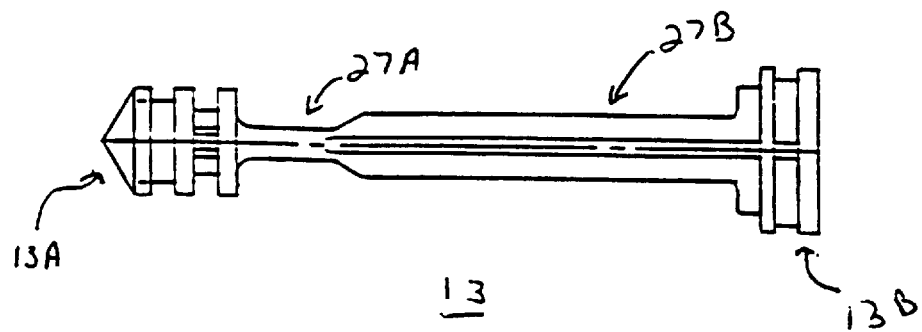
FIG. 9 is an isolated view of a preferred embodiment of the plunger of the present invention.

Referring to FIG. 1, the present invention is a pistol grip applicator 1 that has particular use as a drench gun or syringe for multi-dose administration of fluids such as medications, vitamins, nutrients, growth prometant and/or other remedial or preventive compositions.

The applicator 1 comprises: a body, a needle assembly, a dosage tube, a plunger assembly and a bottle locking assembly. In a preferred embodiment the body comprises a rear body portion 3 and front body portion 5 and the needle assembly comprises a locking nut 7 and a needle 9.

The rear body portion 3 is preferably molded in two halves from a high impact plastic material such as acrylonitrile butadiene styrene (ABS), acetal or nylon. The two halves may be joined together by any type of fastening means known in the art such as screws or rivets 4.

The front body portion 5 is preferably molded in a single piece from a high impact plastic material such as ABS, acetal or nylon. The front body portion 5 is slidably mounted between the two halves of the rear body portion 3. The front body portion 5 further comprises a nose 35 and an intake mount 24.

The exterior of the nose 35 is threaded to receive a locking nut 7. Locking nut 7 secures a needle 9 or drench tube (not shown) to the applicator.

The interior of nose 35 comprises a passageway 22 which further comprises an injection spring 33, an injection valve 37 and an injection O-ring 39. Passageway 22 is attached to a dosage tube 11 by means of passageway 26.

Dosage tube 11 is made from a clear material such as glass, acrylic or polycarbonate. Dosage tube 11 may comprise volumetric or calibration markings which will enable the operator of the applicator 1 to accurately determine and/or vary the amount of fluid to be delivered by the applicator. In an alternate embodiment, the volume of the dosage tube 11 can be controlled by placing stops at various locations in the housing assembly, preferably in the rear body portion 3, which will allow the front body portion 5 to move a predetermined distance and thereby control drug intake into the dosage tube 11. In the alternate embodiment the stops are preferably located at locations which allow the drug dosage to be metered in 0.5 ml increments.

Figure 10:
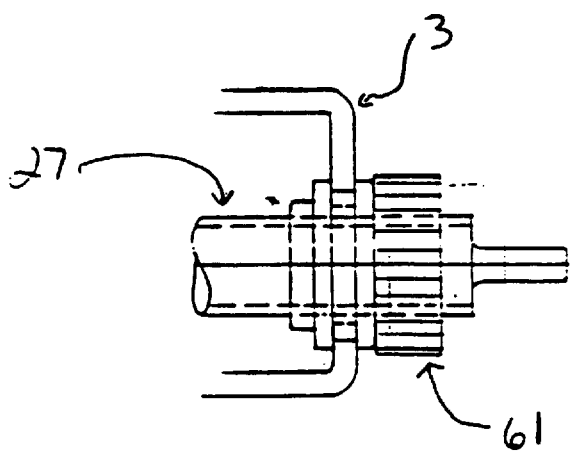
FIG. 10 is an isolated view of a means for adjusting the amount of drug to be delivered by a preferred embodiment of the present invention.

In another embodiment of the present invention and as shown in FIG. 10, the volume of dosage tube 11 may be controlled by adjusting the position of the plunger 13. Specifically, the position of the plunger 13 is varied by rotating a locking nut 61 which is threadably attached to a threaded portion of the plunger shaft 27. The threaded portion of shaft 27 preferably extends through an aperture in the rear of the rear body portion 3.

Plunger 13 is slidably mounted within dosage tube 11. Plunger 13 is attached to the rear body portion 3 by shaft 27. Plunger 13 moves towards the front of dosage tube 11 and thereby displaces the fluid in dosage tube 11 when the operator of the applicator squeezes the front body portion 5 towards the rear body portion 3. Once the operator releases the compressive force applied to the front body portion 5, springs 29 and 31 exert an expansion force on the front body portion 5 causing the plunger 13 to move towards the rear of dosage tube 11.

The shaft 27 preferably comprises a portion with a thin diameter 27A and a portion with a thick diameter 27B. The thin portion 27A of shaft 27 is preferably located towards the plunger head 13A and is either integrally formed or attached to the plunger head 13A by means commonly known in the industry. The thick portion 27B of shaft 27 is preferably integrally formed with the thin section 27A of shaft 27 by techniques commonly known in the art such as injection molding. The thin portion 27A comprises less than 50% of the total length of shaft 27, preferably about 5% to about 35% of the total length of shaft 27. The width or diameter of the thin portion 27A is about 20% to about 70%, preferably 40% to 60%, of the width or diameter of the thick portion 27B.

In a preferred embodiment the plunger assembly is approximately 2.7 inches in length, with the thin portion 27A of shaft 27 comprising approximately 0.38 inches of the length and the thick portion 27B comprising approximately 1.6 inches of the length. The remaining length of the plunger comprising the plunger head 13A and plunger base 13B.

In the preferred embodiment a vertical cross section of the shaft 27 is X shaped although other vertical cross sectional shapes such as circles, squares or triangle are possible. In the preferred embodiment the width of the vertical cross section of the thin portion 27A of shaft 27 is about 0.430 inches and the width of the thick portion 27B of shaft 27 is about 0.505 inches.

It is important that the thin portion 27A can flex and thereby allow the plunger 13 to compensate for any misalignment with dosage tube 11.

In a preferred embodiment the plunger 13 is integrally formed with shaft 27 from polycarbonate or other suitable thermoplastic material which will impart the required flexibility and memory to shaft 27.

The intake mount 24 is connected to passageway 26 by passageway 28. Preferably, the intake mount 24 and passageway 28 are connected to the applicator and passageway 26 at an angle between about 90° and about 70° and most preferably about 90° to about 80°.

The interior of the intake mount 24 comprises an intake spring 25 and an intake valve 30 which control the flow of fluid from the drug or fluid supply bottle 41 into dosage tube 11.

Mounted on the top of the intake mount is the bottle locking assembly 14. The bottle locking assembly 14 comprises a supply needle assembly 15, a locking ring 17 and a bottle holder 19.

The supply needle assembly 15 further comprises: a fluid intake needle 15b, one end of which is connected to the intake valve 30 and the other end is placed in the fluid supply bottle 41; an air intake needle 15a, one end is connected to an air valve 23 and the other end is located so that air can be provided to the fluid supply bottle 41 when the fluid is being drawn from the fluid supply bottle 41 through the intake needle 15b and into the dosage tube 11; and a gasket 21 which rests on the needle mounting block 32.

The gasket 21 is preferably rubber but it can be made from other materials commonly known in the industry. The gasket 21 provides a seal between the fluid supply bottle 41 and the needle mounting block 32. Needles 15a, 15b and needle mounting block 32 are preferably made from stainless steel although other material such as chrome plated steel, electroless nickel plated brass or plastics such as ABS may also be used.

Air intake valve 30 and injection valve 37 are preferably made from rubber but other similar substances such as silicone may be used.

The locking ring 17 comprises a side wall 49, an end wall 50 with an aperture 48 and protrusions 51 which extend inwardly from the side wall 49 of the locking ring 17. The aperture 48 allows the supply needle assembly 15 to pass through the locking ring 17. Preferably three, four or more protrusions 51 extend inwardly from the side wall 49 of locking ring 17. The protrusions 51 are spaced equally apart around the inner circumference of the side wall 49. The locking ring is preferably made from an impact resistant plastic such as ABS, styrene or acetal.

The bottle holder 19 comprises: a base 47 with an aperture 52 to allow the supply needle assembly 15 to pass through the base 47 of the bottle holder 19; mounting blocks 46 which are strategically placed on the base 47 to support the supply needle assembly 15; an annular rim 44 which depends downwardly from the base 47 and extends through aperture 48 in end wall 50 of locking ring 17 to function in part as a axial for rotating the locking ring 17; and a plurality of flanges 45 which extend upwardly from the base 47.

Flanges 45 are attached to the base 47 by way of a living hinge which is preferably created by molding base 47 and flanges 45 in one piece from a resilient high impact plastic resin such as ABS, acetal or nylon. At least two flanges 45 are required to properly attach the fluid supply bottle 41 but three or four flanges are preferred.

In a preferred embodiment, flanges 45 extend upwardly from the base 47 and terminate in a bottle holding projection 43 which extends inwardly from the top of the flange 45. It is preferred that the bottle holding projection extend from flange 45 at an angle between 90° and 180°, most preferably about 135°, so that when a drug supply bottle is being attached to the applicator 1, projections 43 exert a downward force on the drug supply bottle causing it to contact gasket 21.

The bottle holder 19 is sized to fit inside the locking ring 17 and more particularly the bottle holder 19 is sized so that the annular rim 44 extends through aperture 48 in the end wall 50 of the locking ring 17 and acts as an axial for rotating the locking ring 17 around the bottle holder 19. The bottle holder 19 is also sized so that the diameter or distance from one end of a bottle holding projection 43 to the opposite or counter bottle holder projection 43, when the flanges 45 are in their normal or uncompressed state, is approximately equal to the outer diameter of the neck of a conventional drug supply bottle.

Protrusions 51 are sized so that when the locking ring 17 is rotated about the bottle holder assembly 19, protrusions 51 contact flanges 45 of bottle holder 19 and force flanges 45 toward the interior of bottle holder 19. It is preferred that protrusions 51 extend inwardly from the side wall 49 so that they exert enough pressure on flanges 45 to enable flanges 45 to compress around the neck of the fluid supply bottle 41 and firmly hold the fluid supply bottle 41 in the bottle locking assembly 14.

If the locking ring 17 is rotated further around the bottle holder 19, protrusions 51 of the locking ring 17 disengage from flanges 45, thereby allowing flanges 45 to return to their normal position and release the fluid supply bottle 41.

In a preferred embodiment the dimensions of the bottle locking assembly 14 are as follows:

| for the locking ring 17: | |
| --- | --- |
| diameter of aperture 48 | 0.701 inches; |
| diameter of end wall 50 | 1.230 inches; |
| thickness end wall 50 | 0.090 inches; |
| height of side wall 49 | 1.050 inches; |
| thickness of protrusion 51* | 0.156 inches; |
| for the bottle holder 19: | |
| diameter of base 47 | 0.690 inches; |
| diameter of aperture 52 | 0.380 inches; |
| height of annular rim 44 | 0.170 inches; |

-continued

| outer radius of annular rim 44 | 0.345 inches; |
| --- | --- |
| height of flange 45 | 0.929 inches; |
| thickness of projection 43 | 0.107 inches. |

*protrusion 51 taper or increase in thickness from the bottom to the top of the locking ring.

Preferably the number of protrusions 51 on the locking ring 17 are equal to the number of flanges 45 on the bottle holder 19. Most preferably the number of protrusions 51 and flanges 45 is three or four. It is preferred that protrusions 51 are equally spaced around the interior circumference of the side wall 50 and flanges 45 are equally spaced around the outer circumference of the base 47 so that as the locking ring 17 is rotated around the bottle holder 19 each protrusion 51 contacts a flange 45 at approximately the same time and the protrusions 51 disengage from the flanges 45 at approximately the same time.

It is preferred that protrusions 51 contact flanges 45 every quarter or third of a rotation of the locking ring 17 about the bottle holder 19 but other fractions of a complete rotation are possible.

In practice, the operator of the applicator 1 attaches the fluid supply bottle 41 to the applicator 1 by first rotating the locking ring 17 to a position where protrusions 51 are disengaged from flanges 45. The operator then centers the rubber stopper of the fluid supply bottle 41 over the supply needle assembly 15. The operator exerts pressure on the fluid supply bottle 41 so that the supply needle assembly 15 pierces the center of the rubber stopper and continues to exert pressure on the fluid supply bottle 41 until the lip 60 of the fluid supply bottle 41 is below projections 43 and the gasket 21 is compressed between the top of the fluid supply bottle 41 and the needle mounting block 32.

Once the gasket 21 is compressed the operator rotates the locking ring 17 a quarter turn clockwise until protrusions 51 engage flanges 45, thereby compressing flanges 45 around the neck of the fluid supply bottle 41 and securing the fluid supply bottle 41 to the applicator 1.

Once the fluid supply bottle 41 is attached to the applicator 1, the operator compresses the front body portion 5 towards the rear body portion 3 of the applicator 1 thereby expelling the air or fluid in dosage tube 11 through nose 35. When the operator releases the compressive force on the front body portion 5, springs 29 and 31 cause the front body portion 5 to return to its original position. As the front body portion 5 returns to its original position, a suction is created by the movement of plunger 13 in dosage tube 11 which in turn causes injection valve 37 to close and intake valve 30 to open. When intake valve 30 opens the suction created by plunger 13 draws the fluid from the fluid supply bottle 41 through needle 15b, passageway 28, passageway 26 and into dosage tube 11.

As the fluid is being withdrawn from the fluid supply bottle 41 into dosage tube 11, air valve 23 is opened to allow air to pass through needle 15a into the fluid supply bottle 41.

Once the correct amount of fluid has entered dosage tube 11, intake valve 30 will close. The operator will inject the animal with needle 9 and then compress the front body portion 5 toward the rear body portion 3 causing plunger 13 to force the fluid out of dosage tube 11, through passageway 26, injection valve 37, passageway 22, needle 9 and finally into the animal.

The needle 9 is then withdrawn from the animal and the operator releases the pressure on the front body portion 5 of the applicator 1, allowing the fluid from the fluid supply bottle 41 to flow into dosage tube 11 as described above so that the next animal may be injected.

The process continues until the fluid supply bottle 41 is empty. When the fluid supply bottle 41 is empty, the operator rotates the locking ring 17 clockwise by a quarter turn to disengage protrusions 51 from flanges 45 and allow flanges 45 to expanded to their normal position. The empty fluid supply bottle 41 is then removed from the supply needle assembly 15 and bottle holder 19 and a new bottle 41 is attached as described above.

Many variations of the present invention will suggest themselves to those skilled in this art in light of the above, detailed description. For example, the various parts of the applicator have been described as being made from high impact plastic, however, in theory any of the various parts could be made from metal or any combination of metal and plastic. All such obvious modifications are within the full intended scope of the appended claims.

All the above mentioned patents, publications and test methods are herein incorporated by reference.

We claim:

1. In a multi-dose applicator including: a body comprising a front portion and a rear portion wherein the front portion is slidably connected to the rear portion; a needle assembly attached to the front portion of the body; a dosage tube attached to the front portion of the body and connected to the needle assembly by a passageway within the front portion of the body; wherein the improvement comprises:
   (i) a bottle locking assembly attached to either the front or rear portion of the body and comprising:
      (a) a locking ring comprising: a side wall; an end wall with an aperture in the end wall; and protrusions that extend inwardly from the side wall;
      (b) a bottle holder that is sized to fit within the side wall of the locking ring and comprising a base with is an aperture and a plurality of flanges that extend upwardly from the base; and
      (c) a supply needle assembly comprising a fluid intake needle for withdrawing fluid from a supply bottle into the dosage tube of the applicator and an air intake needle for providing air to the supply bottle, wherein the locking ring rotates around the bottle holder and the protrusions of the locking ring contact and compress the flanges of the bottle holder to secure the supply bottle to the applicator; and
   (ii) a plunger assembly attached to the rear portion of the body and slidably located within the dosage tube comprising a plunger head and a shaft comprising a thin section and a thick section wherein the plunger head is attached to the thin section of the shaft and the thin section is flexible.

2. In a multi-dose applicator including: a body comprising a front portion and a rear portion wherein the front portion is slidably connected to the rear portion; a needle assembly attached to the front portion of the body; a dosage tube attached to the front portion of the body and connected to the needle assembly by a passageway within the front portion of the body; a plunger assembly attached to the rear portion of the body and slidably located within the dosage tube; wherein the improvement comprises a bottle locking assembly attached to either the front or rear portion of the body and comprising:
   (a) a locking ring comprising: a side wall; an end wall with an aperture in the end wall; and protrusions that extend inwardly from the side wall and are equally spaced round the inner circumference of the locking ring side wall;
   (b) a bottle holder that is sized to fit within the side wall of the locking ring and comprising a base with an aperture and a plurality of flanges that extend upwardly from the base wherein the flanges are equally spaced around the outer circumference of the bottle holder and further wherein the number of flanges equals the number of protrusions on the inner circumference of the locking ring side wall; and
   (c) a supply needle assembly comprising a fluid intake needle for withdrawing fluid from a supply bottle into the dosage tube of the applicator, wherein the locking ring rotates around the bottle holder and the protrusions of the locking ring contact and compress the flanges of the bottle holder to secure the supply bottle to the applicator.

3. The applicator as defined in claim 2 wherein the number of protrusions is three and the number of flanges is three.

4. The applicator as defined in claim 2 wherein the number of protrusions is four and the number of flanges is four.

5. The applicator as defined in claim 2 wherein the protrusions contact the flanges every fraction of a rotation of the locking ring.

6. The applicator as defined in claim 5 wherein the protrusions contact the flanges every half, third or quarter rotation of the locking ring.

7. The applicator as defined in claim 2 wherein each flange comprises an inwardly directed projection at the end of the flange opposite the end attached to the base of the bottle holder.

8. The applicator as defined in claim 7 wherein the inwardly directed projection extends from the flange at an angle between 90° and 180°.

9. The applicator as defined in claim 8 wherein the inwardly directed projection extends from the flange at an angle of about 135°.

* * * * *